(12) United States Patent
Solacroup et al.

(10) Patent No.: US 10,526,631 B1
(45) Date of Patent: Jan. 7, 2020

(54) METHOD OF REDUCING SERINE FOR ASPARAGINE MISINCORPORATION

(71) Applicant: Ares Trading S.A., Aubonne (CH)

(72) Inventors: Thomas Solacroup, Blonay (CH); Matthieu Stettler, Vucherens (CH); Hervé Broly, Chatel-St-Denis (CH)

(73) Assignee: ARES TRADING S.A., Aubonne (CH)

( * ) Notice: Subject to any disclaimer, the term of this patent is extended or adjusted under 35 U.S.C. 154(b) by 141 days.

(21) Appl. No.: 15/457,597

(22) Filed: Mar. 13, 2017

Related U.S. Application Data

(60) Provisional application No. 62/308,624, filed on Mar. 15, 2016.

(51) Int. Cl.
*C12P 21/02* (2006.01)
*C07K 16/24* (2006.01)

(52) U.S. Cl.
CPC ............ *C12P 21/02* (2013.01); *C07K 16/241* (2013.01); *C07K 2317/14* (2013.01); *C07K 2317/51* (2013.01); *C07K 2317/515* (2013.01)

(58) Field of Classification Search
CPC ... C12P 21/02; C07K 16/241; C07K 2317/51; C07K 2317/515; C07K 2317/14
See application file for complete search history.

(56) References Cited

U.S. PATENT DOCUMENTS

2013/0096283 A1\* 4/2013 Khetan ................... C12P 21/02
530/387.9

OTHER PUBLICATIONS

American Type Culture Collection catalog, Formulation for DMEM:F-12 Medium, p. 1, 2019.*

\* cited by examiner

*Primary Examiner* — Delia M Ramirez
(74) *Attorney, Agent, or Firm* — Fox Rothschild LLP

(57) ABSTRACT

The present invention relates to a method of reducing serine for asparagine misincorporation in a protein produced by a culture of cells in a cell culture method, the method comprising the addition of asparagine and iron to the cell culture medium.

22 Claims, 4 Drawing Sheets
Specification includes a Sequence Listing.

Figures

```
                       SEQUENCE LISTING

<160> NUMBER OF SEQ ID NOS: 10

<210> SEQ ID NO 1
<211> LENGTH: 107
<212> TYPE: PRT
<213> ORGANISM: Artificial Sequence
<220> FEATURE:
<223> OTHER INFORMATION: adalimumab light chain variable region

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: adalimumab heavy chain variabe region

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45
```

```
Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
            115                 120
```

```
<210> SEQ ID NO 3
<211> LENGTH: 9
<212> TYPE: PRT
<213> ORGANISM: Artificial Sequence
<220> FEATURE:
<223> OTHER INFORMATION: adalimumab light chain variable region CDR3
<220> FEATURE:
<221> NAME/KEY: misc_feature
<222> LOCATION: (9)..(9)
<223> OTHER INFORMATION: Xaa can be any naturally occurring amino acid

<400> SEQUENCE: 3

Gln Arg Tyr Asn Arg Ala Pro Tyr Xaa
1               5
```

```
<210> SEQ ID NO 4
<211> LENGTH: 12
<212> TYPE: PRT
<213> ORGANISM: Artificial Sequence
<220> FEATURE:
<223> OTHER INFORMATION: adalimumab heavy chain variable region CDR3
<220> FEATURE:
<221> NAME/KEY: misc_feature
<222> LOCATION: (12)..(12)
<223> OTHER INFORMATION: Xaa can be any naturally occurring amino acid

<400> SEQUENCE: 4

Val Ser Tyr Leu Ser Thr Ala Ser Ser Leu Asp Xaa
1               5                   10
```

```
<210> SEQ ID NO 5
<211> LENGTH: 7
<212> TYPE: PRT
<213> ORGANISM: Artificial Sequence
<220> FEATURE:
<223> OTHER INFORMATION: adalimumab light chain variable region CDR2

<400> SEQUENCE: 5

Ala Ala Ser Thr Leu Gln Ser
1               5
```

```
<210> SEQ ID NO 6
<211> LENGTH: 17
<212> TYPE: PRT
<213> ORGANISM: Artificial Sequence
<220> FEATURE:
<223> OTHER INFORMATION: adalimumab heavy chain variable region CDR2

<400> SEQUENCE: 6

Ala Ile Thr Trp Asn Ser Gly His Ile Asp Tyr Ala Asp Ser Val Glu
1               5                   10                  15

Gly
```

```
<210> SEQ ID NO 7
<211> LENGTH: 11
<212> TYPE: PRT
<213> ORGANISM: Artificial Sequence
<220> FEATURE:
<223> OTHER INFORMATION: adalimumab light chain variable region CDR1

<400> SEQUENCE: 7

Arg Ala Ser Gln Gly Ile Arg Asn Tyr Leu Ala
1               5                   10

<210> SEQ ID NO 8
<211> LENGTH: 5
<212> TYPE: PRT
<213> ORGANISM: Artificial Sequence
<220> FEATURE:
<223> OTHER INFORMATION: adalimumab heavy chain variable region CDR1

<400> SEQUENCE: 8

Asp Tyr Ala Met His
1               5

<210> SEQ ID NO 9
<211> LENGTH: 321
<212> TYPE: DNA
<213> ORGANISM: Artificial Sequence
<220> FEATURE:
<223> OTHER INFORMATION: adalimumab light chain variable region

<400> SEQUENCE: 9
gacatccaga tgacccagtc tccatcctcc ctgtctgcat ctgtagggga cagagtcacc        60
atcacttgtc gggcaagtca gggcatcaga aattacttag cctggtatca gcaaaaacca       120
gggaaagccc ctaagctcct gatctatgct gcatccactt tgcaatcagg ggtcccatct       180
cggttcagtg gcagtggatc tgggacagat ttcactctca ccatcagcag cctacagcct       240
gaagatgttg caacttatta ctgtcaaagg tataaccgtg caccgtatac ttttggccag       300
gggaccaagg tggaaatcaa a                                                  321

<210> SEQ ID NO 10
<211> LENGTH: 363
<212> TYPE: DNA
<213> ORGANISM: Artificial Sequence
<220> FEATURE:
<223> OTHER INFORMATION: adalimumab heavy chain variable region

<400> SEQUENCE: 10
gaggtgcagc tggtggagtc tgggggaggc ttggtacagc ccggcaggtc cctgagactc        60
tcctgtgcgg cctctggatt caccttfgat gattatgcca tgcactgggt ccggcaagct       120
ccagggaagg gcctggaatg ggtctcagct atcacttgga atagtggtca catagactat       180
gcggactctg tggagggccg attcaccatc tccagagaca acgccaagaa ctccctgtat       240
ctgcaaatga acagtctgag agctgaggat acggccgtat attactgtgc gaaagtctcg       300
taccttagca ccgcgtcctc ccttgactat tggggccaag gtaccctggt caccgtctcg       360
agt                                                                     363
```

METHOD OF REDUCING SERINE FOR ASPARAGINE MISINCORPORATION

BACKGROUND OF THE INVENTION

Substitution of amino acids during the manufacture of protein sequences is known to occur during protein translation or transcription. A mutation may occur in a DNA sequence, which causes the codon to change leading to the incorporation of the incorrect amino acid at that position during translation of the protein.

Furthermore, substitutions have been found to occur during protein synthesis caused by translation errors despite the fact that transcription correctly occurred. The translation error may result from the misreading of a (correct) DNA sequence or mischarging of a tRNA. This phenomenon has been reported in *E. coli* cells. More recently, the misincorporation of serine at asparagine positions in recombinant proteins expressed in Chinese hamster ovary (CHO) cells has been reported (Wen et al., Journal of Biological Chemistry, (2009) 284: 32686-94.)

Misincorporation can affect the ultimate folding and functionality of the protein that has the misincorporated amino acids present within its peptide sequence. Misincorporation can be determined by various methods known in the art, such as: intact measurement, peptide mapping analysis, or mass spectroscopy sequencing.

Wen et al. discovered that the substitution of serine at asparagine positions was due to the starvation of asparagine in a cell culture medium and that misincorporation could be limited by supplementing the medium with asparagine.

SUMMARY OF THE INVENTION

The present invention provides a cell culture method of reducing serine for asparagine misincorporation in a recombinant protein produced by a culture of cells in a cell culture medium, the method comprising supplementing the cell culture medium with asparagine and iron, the misincorporation of serine for asparagine in the protein produced by the culture of cells is reduced.

In an embodiment of the present invention, cell viability is maintained at a level of at least 80%. In an embodiment of the present invention, the cell culture method has a duration of up to 18 days. In an embodiment of the present invention, the cell culture is a fed batch culture. In an embodiment of the present invention, the concentration of asparagine in the cell culture medium is between about 8 mM and about 15 mM at day 0 of the cell culture method. In an embodiment of the present invention, the concentration of asparagine in the cell culture medium is about 12.5 mM or about 18.5 mM at day 0 of the cell culture method. In an embodiment of the present invention, the concentration of iron in the cell culture medium is between about 1.0 mg/L and about 5.0 mg/L of culture medium, at day 0 of the cell culture method. In an embodiment of the present invention, the concentration of iron in the cell culture medium is about 3.0 mg/L of culture medium, at day 0 of the cell culture method. In an embodiment of the present invention, the cell culture medium is supplemented with asparagine and/or iron at one or more of day 3, 4, 5, 6, 7, 8, 9, 10, 11, 12, 13 or 14 of the cell culture method. In an embodiment of the present invention, the cell culture medium is supplemented on day 3 with asparagine to a concentration of between about 2.0 mM to about 4.5 mM, in addition to any asparagine already present in the cell culture medium. In an embodiment of the present invention, the cell culture medium is supplemented on day 3 with asparagine to a concentration of about 2.3 mM or about 3.5 mM, in addition to any asparagine already present in the cell culture medium. In an embodiment of the present invention, the cell culture medium is supplemented on day 3 with iron to a concentration of between about 0.5 mg/L and about 2.0 mg/L, in addition to any iron already present in the cell culture medium. In an embodiment of the present invention, the cell culture medium is supplemented on day 3 with iron to a concentration of about 0.9 mg/L or about 1.5 mg/L, in addition to any iron already present in the cell culture medium. In an embodiment of the present invention, the cell culture medium is supplemented on day 5 with asparagine to a concentration of between about 4.5 mM and about 8.0 mM, in addition to any asparagine already present in the cell culture medium. In an embodiment of the present invention, the cell culture medium is supplemented on day 5 with asparagine to a concentration of about 4.8 m or about 6.9 mM, in addition to any asparagine already present in the cell culture medium. In an embodiment of the present invention, the cell culture medium is supplemented on one or more of day 5, day 7, and day 10 with iron to a concentration of between about 1.0 mg/L and about 4.0 mg/L, in addition to any iron already present in the cell culture medium. In an embodiment of the present invention, the cell culture medium is supplemented on one or more of day 5, day 7, and day 10 with iron to a concentration of between about 1.7 mg/L or about 3.0 mg/L, in addition to any iron already present in the cell culture medium. In an embodiment of the present invention, the cell culture medium is supplemented on one or more of day 7 and day 10 with asparagine to a concentration of between about 1.0 mM and about 5.0 mM, in addition to any asparagine already present in the cell culture medium. In an embodiment of the present invention, the cell culture medium is supplemented on one or more of day 7 and day 10 with asparagine to a concentration of about 4.8 mM or about 1.7 mM, in addition to any asparagine already present in the cell culture medium. In an embodiment of the present invention, the cell culture medium is serum-free and/or protein-free. In an embodiment of the present invention, the cell culture medium is supplemented with iron together with feed components in a feed medium. In an embodiment of the present invention, the culture of cells comprises CHO cells. In an embodiment of the present invention, cell culture method is carried out in a 3.5 L, 2800 L, 5000 L, or 15,000 L bioreactor. In an embodiment of the present invention, the method further comprises supplementing the cell culture medium with manganese. In an embodiment of the present invention, the method further comprises supplementing the cell culture medium with glucose. In an embodiment of the present invention, the cell culture medium comprises an energy source, essential amino acids, vitamins and/or trace elements. In an embodiment of the present invention, the recombinant protein is a TNFα binding protein. In an embodiment of the present invention, the TNFα binding protein is etanercept or a biosimilar thereof. In an embodiment of the present invention, the TNFα binding protein is an antibody, preferably the antibody is adalimumab, infliximab or a biosimilar thereof, and more preferably the antibody is adalimumab or a biosimilar thereof, wherein the antibody has: (i) a light chain sequence having at least 90% identity with SEQ ID NO:1 and a heavy chain sequence having at least 90% identity with SEQ ID NO:2; (ii) a light chain sequence having at least 95% identity with SEQ ID NO:1 and a heavy chain sequence having at least 95% identity with SEQ ID NO:2; (iii) a light chain sequence of SEQ ID NO:1 and a heavy chain sequence of SEQ ID NO:2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.

The present invention also provides a recombinant protein obtainable by any of the above mentioned methods. In embodiments of the present invention, protein is a TNFα binding protein, preferably the TNFα binding protein is adalimumab, etanercept, or infliximab, more preferably the TNFα binding protein is an adalimumab biosimilar, an etanercept biosimilar, or an infliximab biosimilar, and most preferably the TNFα binding protein is an antibody having: (i) a light chain sequence having at least 90% identity with SEQ ID NO:1 and a heavy chain sequence having at least 90% identity with SEQ ID NO:2; (ii) a light chain sequence having at least 95% identity with SEQ ID NO:1 and a heavy chain sequence having at least 95% identity with SEQ ID NO:2; (iii) a light chain sequence of SEQ ID NO:1 and a heavy chain sequence of SEQ ID NO:2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.

The present invention also provides a pharmaceutical composition comprising any one of the above mentioned recombinant proteins. In embodiments of the present invention, the recombinant protein is an adalimumab biosimilar and preferably the recombinant protein is an antibody having: (i) a light chain sequence having at least 90% identity with SEQ ID NO:1 and a heavy chain sequence having at least 90% identity with SEQ ID NO:2; (ii) a light chain sequence having at least 95% identity with SEQ ID NO:1 and a heavy chain sequence having at least 95% identity with SEQ ID NO:2; (iii) a light chain sequence of SEQ ID NO:1 and a heavy chain sequence of SEQ ID NO:2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.

The present invention also provides a method of making a protein in a cell culture, comprising growing a host cell in a cell culture medium, expressing the protein in the host cell, supplementing the cell culture medium with asparagine and iron, and purifying the protein from the cell culture. In embodiments of the present invention, cell viability is maintained at a level of at least 80% and preferably cell viability is maintained at the level of at least 80% for 18 days. In embodiments of the present invention, the cell culture is a fed batch culture. In embodiments of the present invention, the concentration of asparagine in the cell culture medium is between about 8 mM and about 15 mM at day 0. In embodiments of the present invention, the concentration of asparagine in the cell culture medium is about 12.5 mM or about 18.5 mM at day 0. In embodiments of the present invention, in the concentration of iron in the cell culture medium is between about 1.0 mg/L and about 5.0 mg/L of culture medium, at day 0. In embodiments of the present invention, the concentration of iron in the cell culture medium is about 3.0 mg/L of culture medium, at day 0. In embodiments of the present invention, the cell culture medium is supplemented with asparagine and/or iron at one or more of day 3, 4, 5, 6, 7, 8, 9, 10, 11, 12, 13 or 14. In embodiments of the present invention, the cell culture medium is supplemented on day 3 with asparagine to a concentration of between about 2.0 mM to about 4.5 mM, in addition to any asparagine already present in the cell culture medium. In embodiments of the present invention, the cell culture medium is supplemented on day 3 with asparagine to a concentration of about 2.3 mM or about 3.5 mM, in addition to any asparagine already present in the cell culture medium. In embodiments of the present invention, the cell culture medium is supplemented on day 3 with iron is added to a concentration of between about 0.5 mg/L and about 2.0 mg/L, in addition to any iron already present in the cell culture medium. In embodiments of the present invention, the cell culture medium is supplemented on day 3 with iron to a concentration of about 0.9 mg/L or about 1.5 mg/L, in addition to any iron already present in the cell culture medium. In embodiments of the present invention, the cell culture medium is supplemented on day 5 with asparagine to a concentration of between about 4.5 mM and about 8.0 mM, in addition to any asparagine already present in the cell culture medium. In embodiments of the present invention, the cell culture medium is supplemented on day 5 with asparagine to a concentration of about 4.8 m or about 6.9 mM, in addition to any asparagine already present in the cell culture medium. In embodiments of the present invention, the cell culture medium is supplemented on one or more of day 5, day 7, and day 10 with iron to a concentration of between about 1.0 mg/L and about 4.0 mg/L, in addition to any iron already present in the cell culture medium. In embodiments of the present invention, the cell culture medium is supplemented on one or more of day 5, day 7, and day 10 with iron to a concentration of between about 1.7 mg/L or about 3.0 mg/L, in addition to any iron already present in the cell culture medium. In embodiments of the present invention, the cell culture medium is supplemented on one or more of day 7 and day 10 with asparagine to a concentration of between about 1.0 mM and about 5.0 mM, in addition to any asparagine already present in the cell culture medium. In embodiments of the present invention, the cell culture medium is supplemented on one or more of day 7 and day 10 with asparagine to a concentration of about 4.8 mM or about 1.7 mM, in addition to any asparagine already present in the cell culture medium. In embodiments of the present invention, the cell culture medium is serum-free and/or protein-free. In embodiments of the present invention, the cell culture medium is supplemented with iron together with feed components in a feed medium. In embodiments of the present invention, the host cell is a CHO cell. In embodiments of the present invention, the cell culture method is carried out in a 3.5 L, 2800 L, 5000 L, or 15,000 L bioreactor. In embodiments of the present invention, the method of making further comprises supplementing the cell culture medium with manganese. In embodiments of the present invention, the method of making further comprises supplementing the cell culture medium with glucose. In embodiments of the present invention, the cell culture medium comprises an energy source, essential amino acids, vitamins, and/or trace elements. In embodiments of the present invention, the protein made according to the method is a TNFα binding protein. In embodiments of the present invention, the TNFα binding protein is etanercept or a biosimilar thereof. In embodiments of the present invention, the TNFα binding protein is an antibody, preferably the antibody is adalimumab, infliximab or a biosimilar thereof, and more preferably the antibody is adalimumab or a biosimilar thereof, wherein the antibody has: (i) a light chain sequence having at least 90% identity with SEQ ID NO:1 and a heavy chain sequence having at least 90% identity with SEQ ID NO:2; (ii) a light chain sequence having at least 95% identity with SEQ ID NO:1 and a heavy chain sequence having at least 95% identity with SEQ ID NO:2; (iii) a light chain sequence of SEQ ID NO:1 and a heavy chain sequence of SEQ ID NO:2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.

The present invention also provides recombinant proteins obtainable by any of the above methods of making. In embodiments of the present invention, the recombinant protein is a TNFα binding protein, preferably the TNFα binding protein is adalimumab, etanercept or infliximab, more preferably the TNFα binding protein is an adalimumab biosimilar, an etanercept biosimilar, or an infliximab biosimilar.

The present invention also provides pharmaceutical compositions comprising any one of the above mentioned recombinant proteins.

DETAILED DESCRIPTION

Figure 1:
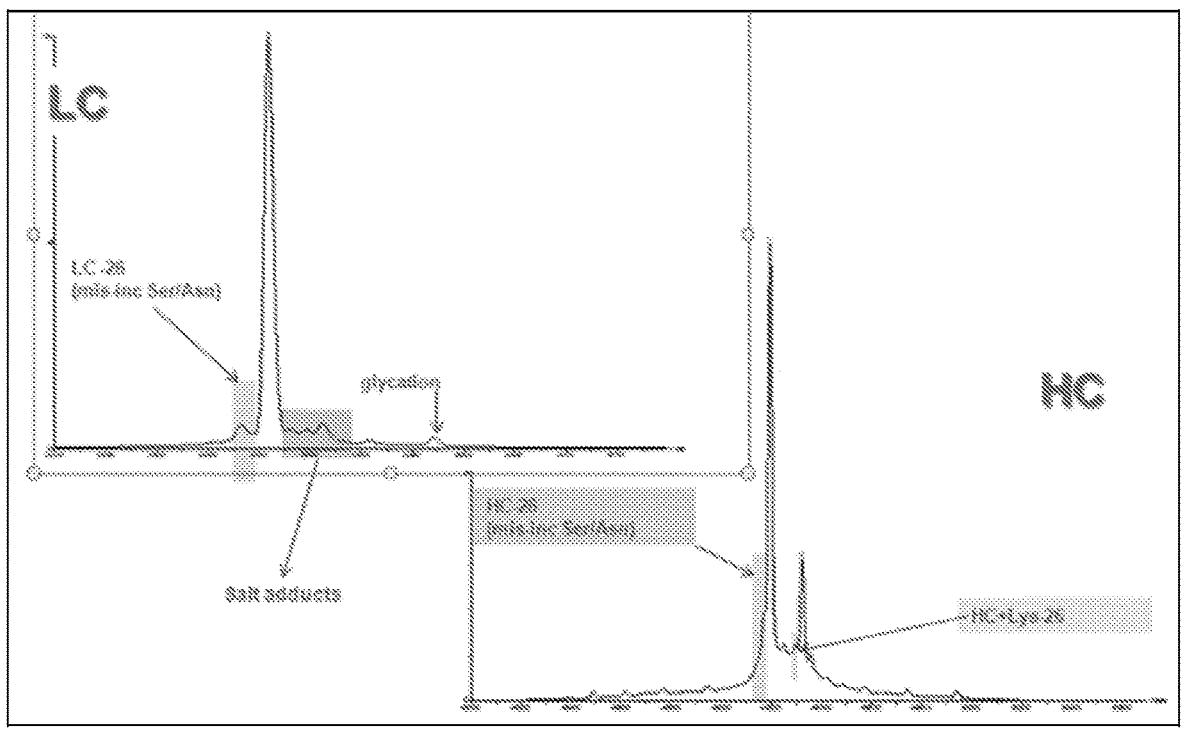
FIG. 1 shows Electrospray Ionisation Mass Spectrometry (ESI-MS) for the adalimumab antibody (Light chain (LC). Heavy chain (HC)) without addition of Asparagine.

The present inventors have found that the supplementation of cell culture medium in a cell culture method with additional asparagine may itself cause a deleterious effect on particular qualities of the resultant recombinant protein and the cells in the cell culture medium.

The nutrients and components in the cell culture medium that are required must be finely balanced in order to make a protein of the correct sequence. The inventors have found that supplementing the medium with asparagine may cause changes to metabolic pathways and processes in the cell culture resulting in lower cell viability and lower quality and/or titre of recombinant protein. However, the inventors have found that adding iron to the medium during the time period that asparagine is added, enables the problem of the misincorporation of serine at the asparagine position to be solved, whilst maintaining the quality and/or titre of the recombinant protein and the viability of the cells in culture.

The present invention provides a cell culture method for reducing serine for asparagine misincorporation in a recombinant protein produced by a culture of cells comprising supplementing the cell culture medium with asparagine and iron. In an embodiment of the present invention, the maintenance of cell viability and/or protein titre and/or protein quality is achieved at a similar level as that of a cell culture method that does not include the addition of asparagine and iron to the culture medium. The present invention also provides a method of producing a protein comprising expressing the protein in a host cell growing in a cell culture medium, supplementing the cell culture medium with asparagine and iron, and purifying the protein from the cell culture medium. In embodiments of the invention, the protein is a recombinant protein, a TNFα binding protein, an antibody, or a TNFα binding antibody, wherein serine for asparagine misincorporation in the protein is reduced.

An embodiment of the present invention provides a cell culture method of reducing serine for asparagine misincorporation in a recombinant protein produced by a culture of cells in a cell culture medium, the method comprising supplementing the cell culture medium with asparagine and iron, wherein the misincorporation of serine for asparagine in the protein produced by the culture of cells is reduced. In an embodiment of the present invention, cell viability is maintained at a level of at least 80% viability (i.e. at least 80% of cells are viable). In an embodiment of the present invention, the initial concentration of asparagine in the cell culture medium is between 8 mM and 20 mM, i.e. the concentration at day 0, of the cell culture process. In an embodiment of the present invention, the he concentration of asparagine in the cell culture medium is between 10 mM and 20 mM at day 0. In an embodiment of the present invention, the concentration of asparagine in the cell culture medium is 12.5 mM at day 0, or 18.5 mM at day 0.

In an embodiment of the present invention, the cell culture method comprises a fed-batch cell culture. In an embodiment of the present invention, the cell culture method has a duration of up to 18 days.

In an embodiment of the present invention, the concentration of iron (ammonium ferric citrate) in the cell culture medium is between 1.0 mg/L and 5.0 mg/L of culture medium at day 0 of the cell culture method, i.e. the initial concentration of iron is between 1.0 mg/L and 5.0 mg/L. In an embodiment of the present invention, the concentration of iron in the cell culture medium is between 2.0 mg/L and 4.0 mg/L of culture medium at day 0, or at 3.0 mg/L at day 0 of the cell culture process.

In an embodiment of the present invention, the cell culture medium is supplemented with asparagine and/or iron at any one or more of day 3, 4, 5, 6, 7, 8, 9, 10, 11, 12, 13 or 14 of the cell culture. In an embodiment of the present invention, the asparagine and iron is added to the cell culture on the same day. In an embodiment of the present invention, the asparagine and iron is added simultaneously. In another embodiment of the present invention, the asparagine and iron is added separately. In another embodiment of the present invention, the asparagine and iron is added to the cell culture on different days. In an embodiment of the present invention, the asparagine and/or iron is added by way of a cell culture feed medium, or as separate supplements.

In an embodiment of the present invention, asparagine is added on day 3, 4 or 5 of the cell culture process to a concentration of between about 2.0 mM and about 4.5 mM, in addition to any asparagine already present in the medium. In an embodiment of the present invention, asparagine is added on day 3 of the cell culture process to a concentration of about 2.3 to about 3.5 mM, in addition to any asparagine already present in the medium or to about 2.3 mM or about 3.5 mM.

In an embodiment of the present invention, iron is added on day 3, 4 or 5 of the cell culture process to a concentration of about 0.5 to about 2.0 mg/L, in addition to any iron already present in the cell culture medium immediately before adding the iron. In an embodiment of the present invention, iron is added day 3 of the cell culture process to a concentration of about 0.9 mg/L to about 1.5 mg/L, in addition to any iron already present in the cell culture medium immediately before adding the iron, or to about 0.9 mg/L or to about 1.5 mg/L.

In an embodiment of the present invention, asparagine is added on day 4, 5, 6, 7, 8, 9, 10 or 11 of the cell culture method to a concentration of between about 4.5 mM and about 8.0 mM, in addition to any asparagine already present in the medium. In an embodiment of the present invention, asparagine is added on day 5, 7 or 10 of the cell culture process to a concentration of between about 4.5 and about 7.4 mM, or to a concentration of about 6.9 mM, or about 4.8 mM, in addition to any asparagine already present in the medium.

In an embodiment of the present invention, iron is added on any one or more of day 4, 5, 6, 7, 8, 9, 10 or 11 of the cell culture process to a concentration of between about 1.5 and about 4.0 mg/L, in addition to any iron already present in the cell culture medium immediately before adding the iron. In an embodiment of the present invention, iron is added on any one or more of day 5, day 7 and day 10 of the cell culture process, to a concentration of about 1.7 mg/L to about 3.0 mg/L or a concentration of about 1.7 mg/L or about 3.0 mg/L, in addition to any iron already present in the cell culture medium immediately before adding the iron.

In an embodiment of the present invention, asparagine is added on any one or more of day 6, 7, 8, 9, 10 or 11 of the cell culture process to a concentration of between about 0.30 mM and about 1.0 mM, in addition to any asparagine already present in the medium. In an embodiment of the present invention, asparagine is added on any one or more of day 7 and day 10 of the cell culture process at a concentration of between about 0.5 and about 0.8 mM, or at a concentration of about 0.7 mM, in addition to any asparagine already present in the medium.

In an embodiment of the present invention, manganese is also added to the culture medium. In an embodiment of the present invention, Manganese (Mn) is added on any one or more of day 3, 4, 5, 6, 7, 8, 9, 10 or 11. In an embodiment of the present invention, no Mn is added prior to day 3. In an embodiment, the medium is Mn free prior to day 3. In an embodiment of the present invention, Mn is added to the culture medium on day 3 to a concentration of about 0.1 µM to about 0.5 µM, in addition to any Mn already present in the medium. In an embodiment of the present invention, Mn is added to the culture medium on day 3 to a concentration of about 0.14 µM to about 0.325 µM, in addition to any Mn already present in the medium. In an embodiment of the present invention, Mn is added to the culture medium on any one of day 5, 7 or day 10 to a concentration of about 0.25 µM to about 1.0 microM, in addition to any Mn already present in the medium. In an embodiment of the present invention, Mn is added to the culture medium on any one of day 5, day 7 or day 10 to a concentration of about 0.29 µM to about 0.75 µM in addition to any Mn already present in the medium.

In an embodiment of the present invention, the recombinant protein is a TNFα binding protein, such as an antibody. In an embodiment of the present invention, the binding protein is etanercept. In an embodiment of the present invention, the antibody is infliximab. In an embodiment of the present invention, the antibody is a biosimilar of etanercept, or infliximab.

In embodiments of the present invention, the antibody has (i) a light chain sequence having at least 90% identity with SEQ ID NO: 1 and a heavy chain sequence having at least 90% identity with SEQ ID NO: 2, or (ii) a light chain sequence having at least 95% identity with SEQ ID NO: 1 and a heavy chain sequence having at least 95% identity with SEQ ID NO: 2, or (iii) a light chain sequence of SEQ ID NO: 1 and a heavy chain sequence of SEQ ID NO: 2. In embodiments of the present invention, the antibody is adalimumab. In embodiments of the present invention, the antibody is a biosimilar of adalimumab. In embodiments of the present invention, the antibody has a light chain sequence comprising SEQ ID NO: 3, SEQ ID NO: 5, and SEQ ID NO: 7; and the antibody has a heavy chain sequence comprising SEQ ID NO: 4, SEQ ID NO: 6, and SEQ ID NO: 8. In embodiments of the present invention, the antibody has a light chain sequence comprising SEQ ID NO: 3, wherein Xaa is any naturally occurring amino acid; and has a heavy chain sequence comprising SEQ ID NO: 4, wherein Xaa is any naturally occurring amino acid. In embodiments of the present invention, Xaa of SEQ ID NO: 3 is Threonine or Alanine. In embodiments of the present invention, Xaa of SEQ ID NO: 4 is Tyrosine or Asparagine.

In embodiments of the present invention, the cell culture medium is serum-free. In embodiments of the present invention, the cell culture medium is protein-free. As used herein "protein-free" means that no protein supplement is included or added to the cell culture medium, such as hydrolysates. The protein that is produced by the cells is, of course, present when it is secreted. In embodiments of the present invention, the cells are CHO cells. In embodiments of the present invention, the cells are CHO-2 cells.

In embodiments of the present invention, the fed-batch culture is carried out in a 3.5 L, 280 L, or 5000 L bioreactor. In embodiments of the present invention, a 15,000 L bioreactor is used.

In embodiments of the present invention, the method further comprises supplementing the cell culture medium with manganese.

In embodiments of the present invention, the cell culture medium comprises one or more of an energy source, essential amino acids, vitamins, and trace elements.

In embodiments of the present invention, the reduction of misincorporation is up to a level of about 50%, about 20%, about 10% of the level of misincorporation that occurs without asparagine and iron supplementation. Preferably there is a 100% reduction of serine residues misincorporated at asparagine positions that is achieved by the method of the present invention.

As mentioned above, it was found that the addition of asparagine to the cell culture medium and/or at subsequent time points during the cell culture method allowed for prevention of the asparagine-serine misincorporation. It was found that concentrations as stated above were sufficient to reduce this misincorporation. However, the addition of asparagine alone has a negative impact on ammonium levels, viability of the cells, and titre of the protein. Furthermore, the quality of the final recombinant protein in terms of the galactosylation profile and the charge profile is vary significantly and negatively impacted in comparison to the recombinant protein having serine misincorporation produced without asparagine addition to the cell culture medium.

The present invention provides a cell culture method for the production of recombinant protein. In particular, the invention provides a method to prevent, minimise, or reduce substitutions of serine for asparagine amino acid residues during translation of a recombinant protein of interest. The invention also provides a method of minimising serine for asparagine misincorporation in a protein, produced in a fed-batch cell culture, comprising the addition of asparagine and iron to the cell culture medium.

The level of misincorporation can be determined by one of skill in the art. The level of serine for asparagine misincorporation is reduced in comparison to a protein produced under the same conditions, with the exception of supplemental asparagine and iron in the cell culture medium. In embodiments of the present invention, the misincorporation of serine for asparagine is reduced to at least 50% of the level of misincorporation that occurs under the same conditions without the addition of iron and asparagine. In embodiments of the present invention, the misincorporation of serine for asparagine is reduced to about 10%, 5%, 4%, 3%, 2%, or 1% of the level of misincorporation that occurs without asparagine and iron supplementation. In embodiments of the present invention, the supplementation of the cell culture with iron and asparagine results in the prevention of serine for asparagine misincorporation altogether, i.e. a 100% reduction.

The present invention provides a cell culture method for the production of recombinant proteins by cell culture. In particular, the invention provides a method of reducing serine for asparagine misincorporation in a recombinant protein produced by a culture of cells, in a cell culture medium optionally in a fed-batch culture, the method comprising supplementing the cell culture medium with asparagine and iron, thereby reducing the misincorporation of serine for asparagine in the protein, i.e. the incorrect incorporation of serine in an asparagine position that occurs during translation of the protein.

The present invention also provides a method of producing a protein that is expressible in a host cell comprising expressing the protein in the host cell growing in a cell culture medium, supplementing the cell culture medium with asparagine and iron, and purifying the protein from the cell culture medium. In embodiments of the present invention, the protein is expressed from a gene that is introduced into the host cell through genetic engineering, i.e. a recombinant protein. In embodiments of the present invention, the protein is one that occurs in nature, or alternatively has a sequence that was engineered or selected by the hand of man. In embodiments of the present invention, the engineered protein is assembled from other protein segments that individually occur in nature, or includes one or more segments that are not naturally occurring.

The present invention also provides a method of producing antibodies and/or other binding proteins comprising expressing the antibody in a host cell growing in a cell culture medium, supplementing the cell culture medium with asparagine and iron, and purifying the antibody from the cell culture medium. In one embodiment, the antibody is a monoclonal antibody.

Particular antibodies can be made, for example, by preparing and expressing synthetic genes that encode the recited amino acid sequences or by mutating human germline genes to provide a gene that encodes the recited amino acid sequences. Moreover, these antibodies can be produced by any method known to one of skill in the art.

In one embodiment, the methods of the invention are used to produce a binding protein and in some embodiments a TNFα binding protein. In one embodiment, the TNFα binding protein is etanercept. In one embodiment, the methods of the invention are used to produce an antibody that specifically binds a tumour-necrosis factor (TNF)-α. In one embodiment, the antibody is adalimumab or infliximab. etanercept. In one embodiment, the antibody has a light chain sequence of SEQ ID NO: 1 and a heavy chain sequence of SEQ ID NO: 2.

Any mammalian cell or cell type that can be cultured and be used for the expression of proteins is utilized in accordance with the present invention. The method of the present invention is applied to the culturing of and expression of recombinant proteins from CHO cell lines. The cell line is CHO-2 cell line.

Additionally, any number of commercially and non-commercially available hybridoma cell lines that express proteins or proteins is utilized in accordance with the present invention.

The mammalian cell culture of the method of the present invention is prepared in any medium suitable for the particular cell being cultured. Commercially available media such as Ham's F10 (Sigma), Minimal Essential Medium ([MEM], Sigma), RPMI-1640 (Sigma), and Dulbecco's Modified Eagle's Medium ([DMEM], Sigma) are exemplary nutrient solutions, as well as any media that are well known to the person skilled in the art. Any of these media is supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin), trace elements (defined as inorganic compounds usually present at final concentrations in the micromolar range) lipids (such as linoleic or other fatty acids) and glucose or an equivalent energy source. Any other necessary supplements may also be included at appropriate concentrations that would be known to those skilled in the art or as defined herein.

In the present invention, the medium is supplemented with asparagine and iron and optionally with manganese. Additional amino acids and nutrients may also be used in accordance with standard cell culture techniques as known to the skilled person, for example to replenish essential amino acids as the cells multiply, replenish an energy source and replenish other essential micronutrients, such as trace elements.

The amount of supplementation required can vary depending on the cellular growth conditions. For example, factors that influence cellular consumption rates, will affect the amount of supplementation that is required to prevent misincorporation and to support normal cell growth. Such factors include, but are not limited to, temperature, osmolality, and pH, as known in the art.

The basal cell culture medium i.e. the medium in which the cell culture is started at day 0, prior to any additional supplementation may contain essential amino acids, vitamins (such as folic acid, biotin, thiamine), salts (such as sodium chloride, sodium bicarbonate), metal ions (for example, in the form of cupric sulphate, ferric ammonium citrate) anti foaming agents (such as Pluronic®) and an energy source (such as glucose or sucrose). The particular combination and amounts of each component may vary depending on the cell line, and the recombinant protein to be produced.

Various methods of preparing mammalian cells for production of proteins or proteins by fed-batch culture are well known in the art. Generally, the cells are first propagated or expanded in a step-wise procedure until a cell density is reached that is suitable for inoculating the bioreactor in which the method of the invention is to take place.

Such methods of propagation or expansion can be carried out by any of the variety of methods well-known to the skilled person.

In accordance with the present invention, the culture size can be any volume that is appropriate for production of recombinant proteins. In one embodiment, the volume of the production bioreactor is at least 500 liters. In other preferred embodiments, the volume of the production bioreactor is 1000, 2000, 2500, 5000, 8000, 10,000, 12,000 or 15,000 litres or more, or any volume in between. One of ordinary skill in the art will be aware of and will be able to choose a suitable culture size for use in practicing the present invention, depending on the titre of recombinant protein required.

In embodiments of the present invention, the cells are allowed to grow for a defined period of time. For example, depending on the starting concentration of the cell culture, the temperature at which the cells are grown, and the intrinsic growth rate of the cells, the cells is grown for 0, 1, 2, 3, 4, 5, 6, 7, 8, 9, 10, 11, 12, 13, 14, 15, 16, 17, 18, 19, 20 or more days. In some cases, the cells are allowed to grow for a month or more. The method of the present invention may involve maintaining the cell culture for a duration 14, 15, 16, 17 or 18 days.

In embodiments of the present invention, the cells are maintained in a subsequent production phase (after the log phase) until a desired cell density or production titre is reached. In one embodiment, the cells are maintained in the subsequent production phase until the titre to the recombinant protein or protein reaches a maximum. In other embodiments, the culture is harvested prior to this point. For example, the cells is maintained for a period of time sufficient to achieve a viable cell density of 1, 5, 10, 15, 20, 25, 30, 35, 40, 45, 50, 55, 60, 65, 70, 75, 80, 85, 90, 95 or 99 percent of maximal viable cell density, and to produce a suitable titre and quality of recombinant protein.

In embodiments of the present invention, the cells are allowed to grow for a defined period of time during the subsequent production phase.

In certain cases, it is necessary to supplement the cell culture during the growth and/or subsequent production phase with nutrients or other medium components that have been depleted or metabolized by the cells. Alternatively or additionally, it is beneficial or necessary to supplement the cell culture prior to the subsequent production phase. As non-limiting examples, it is beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source.

In embodiments of the present invention, amino acids are added to the culture. In particular, in the method of the invention, the amino acid asparagine is added to the culture. However, other amino acids to support cell growth and protein production may also be added to the medium. The amount of the amino acids added to the culture can vary depending on the cells being grown, or other conditions. In the present invention, the amount of asparagine in the basal cell medium (i.e. on day 0) is from about 5 mM to about 20 mM, or from about 10 mM to about 19 mM. The amount of asparagine at day 0 is about 12.5 mM or it is about 18.5 mM. The amount of asparagine added to the culture after day 0 is to a concentration of from about 1 mM to about 10 mM or from about 3.0 mM to about 8.0 mM, in addition to any asparagine already present in the medium. The amount of asparagine added to the culture is to a concentration of from between about 2.0 mM to about 7.0 mM. The asparagine is added to the culture to a concentration of any of about 1.7 mM, about 2.3 mM, about 3.5 mM, about 4.8 mM or about 6.9 mM. In embodiments of the present invention, amino acids are added in the initial culture medium prior to the cell culture process (i.e. at day 0) or else supplemented in the feed media in a fed-batch system, on any one or more of day 1, 2, 3, 4, 5, 6, 7, 8, 9, 10, 11, 12, 13, 14, 15, 16, 17 or 18.

In embodiments of the present invention, metal ions are added to the cell culture medium. In particular, iron is added to the cell culture medium. In embodiments of the present invention, other ions are added to the medium in order to support cell growth and/or protein production. The iron is in the form of ferric ions, such as ferric ammonium citrate. The amount of iron in the basal cell medium, i.e. at day 0 of the cell culture is from about 1.0 mg/L to about 5.0 mg/L, it is at about 1.5 mg/L, 2.0 mg/L, 2.5 mg/L, 3.0 mg/L, 3.5 mg/L, 4.0 mg/L, 4.5 mg/L. The amount of iron in the basal cell medium is about 3.0 mg/L. The amount of ion added to culture after day 0, i.e. as a feed medium or a supplement, is to a concentration of from about 0.5 mg/L to about 5.0 mg/L, or about 1.0 mg/L, about 1.5 mg/L, about 2.0 mg/L, about 2.5 mg/L, about 3.0 mg/L, about 3.5 mg/L, about 4.0 mg/L to about 5.0 mg/L. Iron is added to a concentration of about 0.9 mg/L or about 1.7 mg/L.

In an embodiment, the asparagine and iron (and optionally Mn) are added in accordance with schedule 1 or schedule 2, below.

|  | Day 0 | Day 3 | Day 5 | Day 7 | Day 10 |
| --- | --- | --- | --- | --- | --- |
| Schedule 1 |  |  |  |  |  |
| Iron | 3 mg/L | 6.9 mg/L | 1.7 mg/L | 1.7 mg/L | 1.7 mg/L |
| Asparagine | 8.5 mM | 2.3 mM | 4.8 mM | 4.8 mM | 4.8 mM |
| optional Manganese | — | 0.4 μM | 0.29 μM | 0.29 μM | 0.29 μM |
| Schedule 2 |  |  |  |  |  |
| Iron | 3 mg/L | 1.5 mg/L | 3.0 mg/L | 3.0 mg/L | 3.0 mg/L |
| Asparagine | 1.25 mM | 3.5 mM | 6.9 mM | 1.7 mM | 1.7 mM |
| optional Manganese | — | 0.325 μM | 0.75 μM | 0.75 μM | 0.75 μM |

In embodiments of the present invention, supplementary components, including the amino acids, may all be added to the cell culture at one time, or they are provided to the cell culture in a series of additions. The supplementary components are provided to the cell culture at multiple times in proportional amounts. Alternatively, it may be desirable to provide only certain of the supplementary components initially, and provide the remaining components at a later time. The cell culture is fed at regular intervals with the same concentrations of one or more of the supplementary components.

In embodiments of the present invention, the total volume added to the cell culture is kept to a minimal amount. For example, the total volume of the medium or solution(s) containing the supplementary components added to the cell culture is 1, 2, 3, 4, 5, 6, 7, 8, 9, 10, 15, 20, 25, 30, 35, 40, 45 or 50% of the volume of the cell culture prior to providing the supplementary components. The total volume added is up to 35% of the initial cell culture volume, i.e. the volume at day 0.

In general, it will typically be desirable to isolate and/or purify proteins or polypeptides produced by the method of the present invention. The expressed polypeptide or protein is secreted into the medium and thus cells and other solids are removed, as by centrifugation or filtering for example, as a first step in the purification process. Further purification is carried out by any method known to the skilled person.

The present invention also provides a recombinant protein produced by any of the method described above. The invention also includes an anti-TNFα antibody, produced by the method of the invention e.g., an antibody comprising one or more of the sequences set forth in SEQ ID NOs: 1, or 2 as an antibody comprising or consisting of the light chain set forth in SEQ ID NO: 1 and the heavy chain set forth in SEQ ID NO: 2. In embodiments of the present invention, the antibody is adalimumab or infliximab. In embodiments of the present invention, the antibody is a biosimilar of either adalimumab or infliximab. In embodiments of the present invention, the anti-TNFα antibody is an antibody having at least about 90%, 95%, 98%, or 99% amino acid sequence identity to SEQ ID NO: 1 or SEQ ID NO: 2. A further aspect of the invention provides a basal cell culture medium containing from about 10 mM to about 20 mM asparagine and from about 2 mg/L to about 4 mg/L iron.

Once purified, the recombinant protein or polypeptide (for example an antibody such as an anti-TNFα antibody described herein) can be formulated as a pharmaceutical composition for administration to a subject, e.g., to treat a disorder, such as an autoimmune disorder or disease.

The foregoing description is to be understood as being representative only and is not intended to be limiting. Alternative methods and materials for implementing the invention and also additional applications will be apparent to one of skill in the art, and are intended to be included within the accompanying claims.

Bearing in mind the teachings of Wen et al., the skilled person would assume that supplementing the medium with asparagine would simply solve the problem of serine misincorporating at asparagine positions within a recombinant protein. However, the additional asparagine (despite being added at the minimal amount required to prevent serine misincorporation at the asparagine positions) may lead to a change in the proportional balance of nutrients (amino acids, metal ions, etc), which in turn may have consequential effects on the cell culture, leading to, for example, loss of cell viability, change in charge profile of the protein, change in glycosylation pattern of the protein, reduction in protein titre, etc.). An increase in the ammonium levels in the cell culture medium may also occur.

In order to achieve an acceptable yield and/or titre of recombinant protein at the end of the cell culture period, the cell culture method normally runs from around 14 to 18 days. The addition of asparagine may cause a drop of cell viability before this time point (i.e. prior to day 14 of the cell culture process) and, therefore, additional modifications to the cell culture medium are included in the method of the invention in order to ensure that the cells continue to grow (i.e. remain viable) to the point of producing an acceptable titre of recombinant protein. In order to produce an acceptable titre of protein, the maintenance of cell viability for the duration of the cell culture period is clearly of importance. Other effects that are seen upon the addition of the increased asparagine concentration are changes in the galactosylation profile and the charge profile of the resultant protein. Therefore, a balance of the asparagine required to prevent misincorporation together with compensating adjustment of the other nutrients in order to maintain the characteristics and titre of the final protein product, is provided.

It was unexpectedly found that the addition of iron to the feed medium was able to address these issues, whilst retaining a minimum level of asparagine sufficient to prevent misincorporation of serine at the asparagine positions in the recombinant protein. It was also unexpectedly found that supplementation of asparagine and/or iron on certain days of the cell culture process addressed these issues.

Interestingly, nutrients are normally added to cell culture in concentrations that mirror the rate of growth of the cells i.e. during cell growth phase more nutrients are required (e.g. such as iron) as the levels of such nutrients are depleted by the multiplying cells. As the cells approach a growth plateau, a lower concentration of nutrients is generally expected to be required. However, it was found that asparagine supplementation did not follow this pattern to achieve the optimal results. Therefore, the pattern of feeding of the asparagine to the cell culture media on 1 or more days of the cell culture process is an embodiment of the present invention.

As used herein, the terms "about" and "approximately", as applied to one or more particular cell culture conditions or to the level of misincorporation, refer to a range of values that are similar to the stated reference value for that culture condition or misincorporation level. The term "about" may refer to a range of values that fall within 10 percent or less of the stated reference value for that culture condition or misincorporation level.

The term "amino acid" as used herein refers to any of the twenty naturally occurring amino acids that are normally used in the formation of proteins, or analogs, or derivatives of those amino acids as understood by the skilled person. Amino acids of the present invention are provided in medium to cell cultures. The amino acids provided in the medium are provided as salts or in hydrate form.

The term "to a concentration" it is meant that the amount to be added to the culture medium is calculated on the basis that there is no asparagine and/or iron present in the culture medium. In practice, there are traces of asparagine and/or iron present, if the supplements have not been entirely depleted by the growing cells. However, the supplementation occurs on the assumption that there is no or very little iron or asparagine (or Mn) left at the time that the additional amount is added.

As used herein, "adalimumab" refers to any human monoclonal antibody that specifically binds a tumour-necrosis factor (TNF)-$\alpha$, having the light chain sequence of SEQ ID NO: 1 and the heavy chain sequence of SEQ ID NO: 2. Adalimumab is sold under the trade name Humira® and has CAS designation 33-1731-18-1.

As used herein, "biosimilar" (of an approved reference product/biological drug, such as a protein therapeutic, antibody, etc.) refers to a biologic product that is highly similar to a reference product notwithstanding minor differences in clinically inactive components having no clinically meaningful differences between the biological product and the reference product in terms of the safety, purity, and potency of the product. In one embodiment, the biosimilar biological product is biosimilar to the reference product based upon data derived from (a) analytical studies that demonstrate that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is licensed and intended to be used and for which licensure is sought for the biological product. In one embodiment, the biosimilar biological product and reference product utilize the same mechanism or mechanisms of action for the condition or conditions of use prescribed, recommended, or suggested in the proposed labeling, but only to the extent the mechanism or mechanisms of action are known for the reference product. In one embodiment, the condition or conditions of use prescribed, recommended, or suggested in the labeling proposed for the biological product have been previously approved for the reference product. In one embodiment, the route of administration, the dosage form, and/or the strength of the biological product are the same as those of the reference product. In one embodiment, the facility in which the biological product is manufactured, processed, packed, or held meets standards designed to assure that the biological product continues to be safe, pure, and potent. The reference product may be approved in at least one of the U.S., Europe, or Japan.

The term "antibody" is used as understood in the art, i.e. an immunoglobulin molecule that recognizes and specifically binds to a target (such as a protein, polypeptide, peptide, carbohydrate, polynucleotide, lipid, or combinations of the foregoing) through at least one antigen recognition site within the variable region of the immunoglobulin molecule.

The term encompasses, as understood in the art, intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, monovalent or monospecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be any of IgA, IgD, IgE, IgG, and IgM, and include, for example IgG1, IgG2, IgG3, IgG4, IgAI and IgA2.

The terms "culture" and "cell culture" as used herein refer to a eukaryotic cell population that is suspended in a medium under conditions suitable to survival and/or growth of the cell population. These terms may refer to the combination comprising the mammalian cell population and the medium in which the population is suspended.

The terms "medium", "cell culture medium" and "culture medium" as used herein refer to a solution containing nutrients which nourish growing eukaryotic cells that has not been modified either by supplementation, or by selective removal of a certain component. Typically, these solutions provide essential and non-essential amino acids, vitamins, energy sources, lipids, and trace elements required by the cell for minimal growth and/or survival. The solution may also contain components that enhance growth and/or survival above the minimal rate, including hormones and growth factors. The solution is preferably formulated to a pH and salt concentration optimal for cell survival and proliferation. The medium may also be a "defined medium" such as a serum-free medium and/or protein free medium that contains no proteins, hydrolysates or components of unknown composition. Defined media are free of animal-derived components and all components have a known chemical structure.

The term "batch culture" as used herein refers to a method of culturing cells in which all the components that will ultimately be used in culturing the cells, including the medium as well as the cells themselves, are provided at the beginning of the culturing process i.e. day 0. A batch culture is typically stopped at some point and the cells and/or components in the medium are harvested and generally purified.

The term "bioreactor" as used herein refers to any vessel used for the growth of a mammalian cell culture. The bioreactor can be of any size so long as it is useful for the culturing of mammalian cells. Typically, the bioreactor will be at least 1 litre and is 10, 100, 250, 500, 1000, 2500, 5000, 8000, 10,000, 12,000, 15,000 litres or more, or any volume in between. The internal conditions of the bioreactor are typically controlled during the culturing period. The bioreactor can be composed of any material that is suitable for holding mammalian cell cultures suspended in media under the culture conditions of the present invention, including glass, plastic or metal. The term "production bioreactor" as used herein refers to the final bioreactor used in the production of the protein or protein of interest. The volume of the large-scale cell culture production bioreactor is typically at least 500 liters and is 1000, 2000, 2500, 5000, 8000, 10,000, 12,0000 liters or more, or any volume in between.

The term "cell density" as used herein refers to that number of cells present in a given volume of medium.

The term "fed-batch culture" as used herein refers to a method of culturing cells in which additional components are provided to the culture at some time subsequent to the beginning of the culture process i.e. after day 0. The provided components typically comprise nutritional supplements for the cells which have been depleted during the culturing process. A fed-batch culture is typically stopped at some point and the cells and/or components in the medium are harvested and optionally purified.

The term "growth phase" of the cell culture refers to the period of exponential cell growth (the log phase) where cells are generally rapidly dividing. During this phase, cells are cultured for a period of time, usually between 1-4 days, and under such conditions that cell growth is maximized. The determination of the growth cycle for the host cell can be determined for the particular host cell envisioned without undue experimentation. For a particular cell line, the period of time and conditions are determined to be optimal for cell growth and division. During the growth phase, cells are cultured in nutrient medium containing the necessary additives, in a controlled atmosphere, such that optimal growth is achieved for the particular cell line. Cells are maintained in the growth phase for a period of about between one and four days, usually between two to three days.

The term "production phase" of the cell culture refers to the period of time during which cell growth has plateaued. During the production phase, logarithmic cell growth has ended and protein production is primary. During this period of time the medium is generally supplemented to maintain cell stability.

The term "expression" or "expresses" are used herein to refer to transcription and translation occurring within a host cell. Protein encoded by a product gene can be quantitated either by assaying for the biological activity of the protein or by employing assays that are independent of such activity, such as western blotting or radioimmunoassay using antibodies that are capable of reacting with the protein. Sambrook et al., Molecular Cloning: A Laboratory Manual, pp. 18.1-18.88 (Cold Spring Harbor Laboratory Press, 1989).

The term "protein" as used herein refers to a sequential chain of amino acids linked together via peptide bonds, also referred to interchangeably with the term "polypeptide". The term is used to refer to an amino acid chain of any length, but one of ordinary skill in the art will understand that the term is not limited to lengthy chains and can refer to a minimal chain comprising two amino acids linked together via a peptide bond. If a single protein is the discrete functioning unit and does require permanent physical association with other proteins in order to form the discrete functioning unit. If discrete functional unit is comprised of more than one polypeptide that physically associate with one another, the term "protein" as used herein refers to the multiple polypeptides that are physically coupled and function together as the discrete unit, such as an antibody.

The terms "recombinantly expressed protein" and "recombinant polypeptide or protein" as used herein refers to a protein expressed from a mammalian host cell that has been genetically engineered to express that protein. The recombinantly expressed protein can be identical or similar to proteins that are normally expressed in the mammalian host cell. The recombinantly expressed protein can also be foreign to the host cell (i.e. exogenous). Alternatively, the recombinantly expressed protein can be chimeric in that portions of the protein contain amino acid sequences that are identical or similar to proteins normally expressed in the mammalian host cell, while other portions are foreign to the host cell.

The terms "substitution" or "misincorporation" of an amino acid as used herein refer to incorporation of the incorrect amino acid, based on the genetic sequence of the protein, into the sequence of a protein of interest. For example, serine can be misincorporated into a protein sequence at a point in which asparagine is the correct amino acid to be incorporated, i.e. the codon at that point is one of AAT or AAC.

The term "titre" as used herein refers to the total amount of recombinantly expressed protein or protein produced by a mammalian cell culture divided by a given amount of medium volume. Titre is typically expressed in units of milligrams of protein or protein per milliliter of medium, or grams per litre.

The term "viability" is taken to mean whether a cell is alive or dead. % cell viability is the proportion of cells that are alive in a culture of cells. Tests for cell viability are well known in the art. Viability of 80% means that 80% of cells in a culture are alive i.e. 20% of cells have died.

As used herein, the singular forms "a", "an", and "the" include plural forms unless the context clearly dictates otherwise.

It is understood that whenever embodiments are described herein with the language "comprising" otherwise analogous embodiments described in terms of "consisting" and/or "consisting essentially of" are also provided.

Those of ordinary skill in the art will understand that various modifications to these preferred embodiments are within the scope of the appended claims. It is the claims and equivalents thereof that define the scope of the present invention, which is not and should not be limited to or by this description of certain preferred embodiments.

The invention is exemplified below by way of the following non-limiting examples.

EXAMPLES

All Examples were carried out by expressing a biosimilar of adalimumab.

Example 1

As shown in FIG. 1, in the absence of Asn supplementation, there are misincorporations of Asn-Ser in the light chain (small peak) and in the heavy chain (elbow) of the adalimumab biosimilar.

Figure 2:
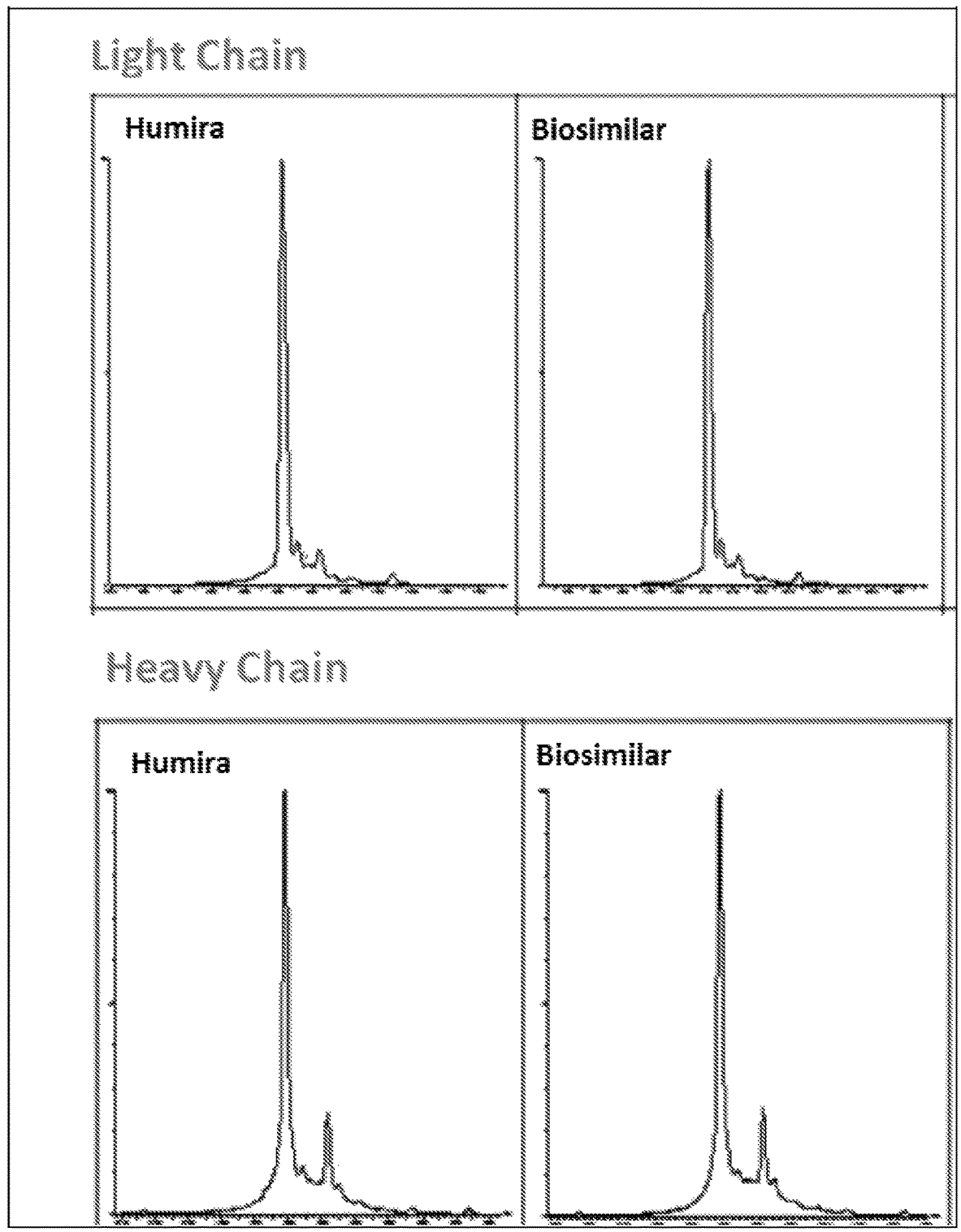
FIG. 2 shows the impact on serine for asparagine misincorporation when supplementing the cell culture with 6 mM asparagine.
Figure 3:
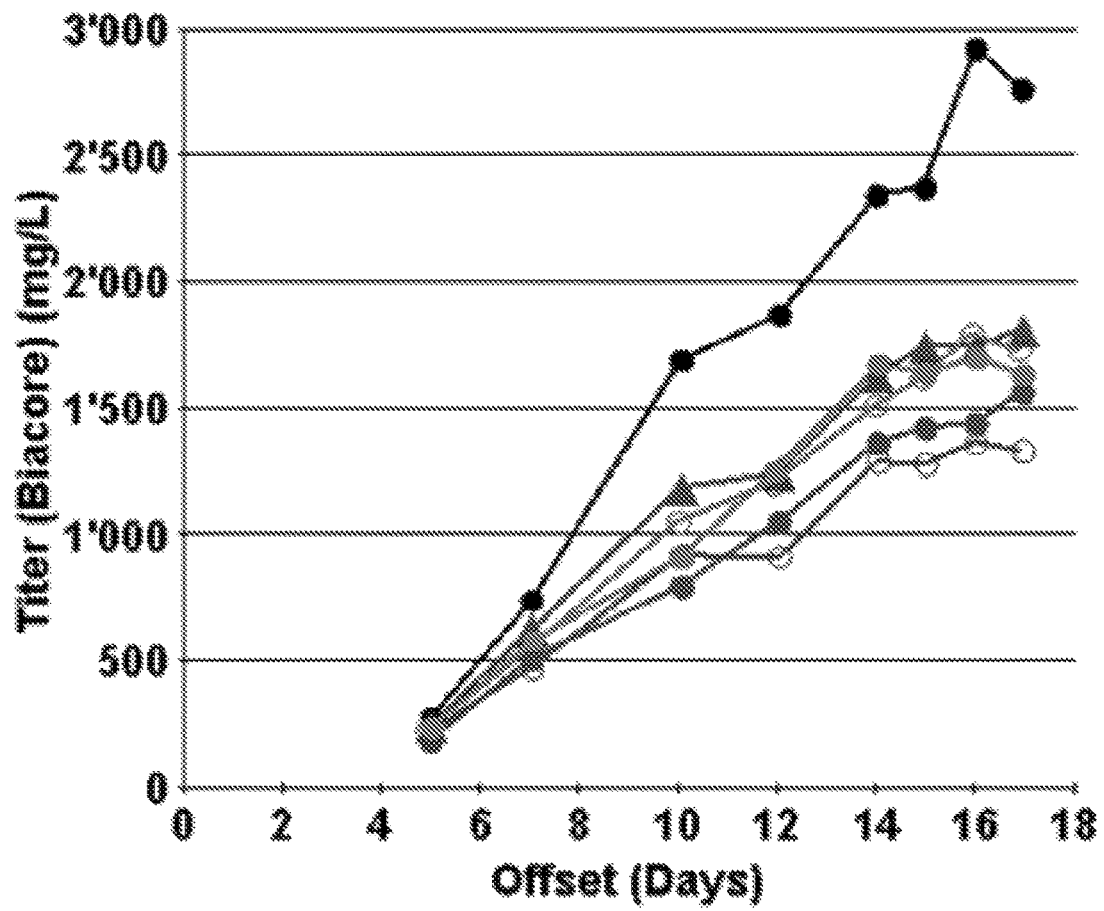
FIG. 3 shows decreased productivity when supplementing the cell culture with Asn as compared to the culture conditions where there was no asparagine supplementation.

The cell culture process was repeated with the addition of 6 mM asparagine to the cell culture. The results are shown in FIG. 2. The biosimilar molecule from the run with addition of 6 mM Asn (FIG. 2) did not show any Asn-Ser misincorporation. The ESI-MS profiles of light and heavy chains were similar to those of the Humira molecule (RMP).

Example 2

It was found that the cells consumed asparagine quickly and so multiphase supplementation strategies were developed and tested:

Strategy 1a=supplementing with 10 mM Asn on day 0 and 2 mM Asn on days 3, 5, 6, 7, and 8;
Strategy 1b=supplementing with 10 mM Asn on day 0 and 5 mM Asn on days 3, 5, 6, 7, and 8;
Strategy 1c=supplementing with 10 mM Asn on day 0 and 8 mM Asn on days 3, 5, 6, 7, and 8;
Strategy 2a=supplementing with boluses of Asn on days 3, 5, 7, 10, and 14 (40 mM Asn total);
Strategy 2b=supplementing with boluses of Asn on days 3, 5 and 7 (40 mM Asn total);
Strategy 3a=supplementing with 18 mM Asn on day 0; 2.3 mM Asn on day 3; and 4.8 mM Asn on days 5, 7, and 10; and
Strategy 3b=supplementing with 12.5 mM Asn on day 0; 3.5 mM Asn on day 3; 6.9 mM Asn on day 5; and 1.7 mM Asn on days 7 and 10.

Strategy 3a and 3b provided the best results and were selected.

Example 3

Figure 4:
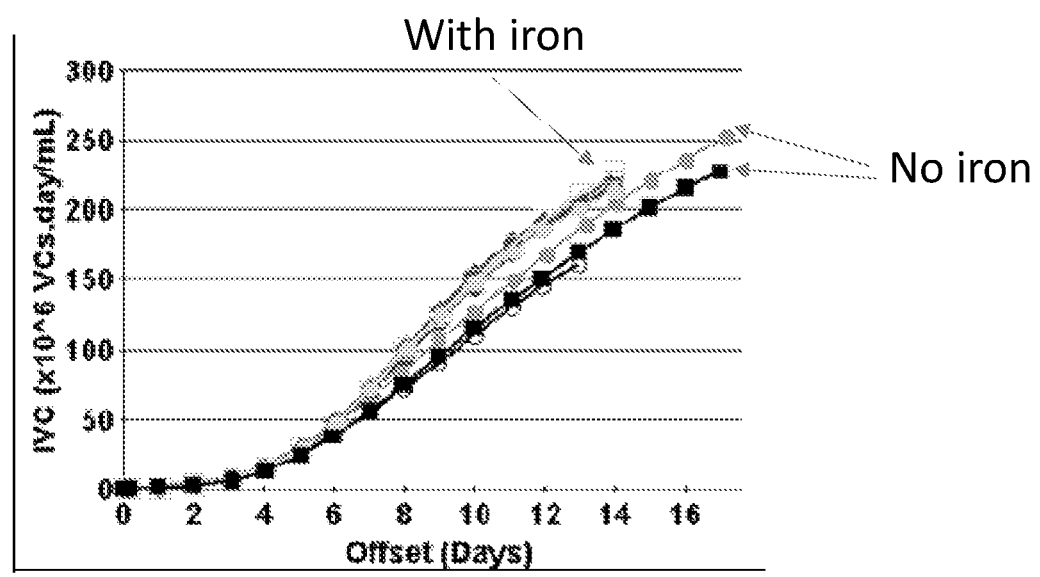
FIG. 4 shows that the maximum cell density and protein expression productivity are increased by adding iron in addition to asparagine without affecting the reduced rate of misincorporation of Asn-Ser.

It was found that by adding iron the maximum cell density could be increased without affecting the rate of misincorporation of Asn-Ser. This improved the productivity which had been reduced by the asparagine supplementation. See FIG. 4.

The concentrations of Asn and Iron in cell culture were as follows:

| Strategy 3A | Day 0 | Day 3 | Days 5, 7, 10 |
|---|---|---|---|
| Asparagine mM | 18.5 | 2.3 | 4.8 |
| Iron (ferric ammonium citrate) mg/L | 3 | 0.9 | 1.7 |

| Strategy 3B | Day 0 | Day 3 | Day 5 | Days 7 and 10 |
|---|---|---|---|---|
| Asparagine mM | 12.5 | 3.5 | 6.9 | 1.7 |
| Iron (ferric ammonium citrate) mg/L | 3 | 1.5 | 3.0 | 3.0 |

What is claimed is:

1. A cell culture method of reducing serine for asparagine misincorporation in a recombinant protein produced by a culture of cells in a cell culture medium, the method comprising supplementing the cell culture medium with asparagine and iron, wherein the concentration of iron in the cell culture medium is between 1.0 mg/L and 5.0 mg/L of culture medium at day 0 of the cell culture method, and wherein the misincorporation of serine for asparagine in the protein produced by the culture of cells is reduced.

2. A method of making a protein in a cell culture, comprising growing a host cell in a cell culture medium, wherein the concentration of iron in the cell culture medium is between 1.0 mg/L and 5.0 mg/L of culture medium at day 0 of the cell culture method, expressing the protein in the host cell, supplementing the cell culture medium with asparagine and iron, and purifying the protein from the cell culture.

3. The method of claim 2, wherein cell viability is maintained at a level of at least 80%.

4. The method of claim 3, wherein cell viability is maintained at the level of at least 80% for 18 days.

5. The method of claim 2, wherein the cell culture is a fed batch culture.

6. The method of claim 2, wherein the concentration of asparagine in the cell culture medium is between 8 mM and 15 mM at day 0.

7. The method of claim 2, wherein the concentration of asparagine in the cell culture medium is 12.5 mM or 18.5 mM at day 0.

8. The method of claim 2, wherein the concentration of iron in the cell culture medium is 3.0 mg/L of culture medium at day 0.

9. The method of claim 2, wherein the cell culture medium is supplemented with asparagine and/or iron at one or more days selected from the group consisting of day 3, day 4, day 5, day 6, day 7, day 8, day 9, day 10, day 11, day 12, day 13 and day 14.

10. The method of claim 2, wherein the cell culture medium is supplemented according to one or more methods selected from the group consisting of:
    (a) on day 3, the cell culture medium is supplemented with asparagine to a concentration of between 2.0 mM to 4.5 mM, in addition to any asparagine already present in the cell culture medium;
    (b) on day 5, the cell culture medium is supplemented with asparagine to a concentration of between 4.5 mM and 8.0 mM, in addition to any asparagine already present in the cell culture medium; and
    (c) on day 7 and/or day 10, the cell culture medium is supplemented with asparagine to a concentration of between 1.0 mM and 5.0 mM, in addition to any asparagine already present in the cell culture medium.

11. The method of claim 2, wherein the cell culture medium is supplemented according to one or more methods selected from the group consisting of:
    (a) on day 3, the cell culture medium is supplemented with asparagine to a concentration of 2.3 mM or 4.5 mM, in addition to any asparagine already present in the cell culture medium;
    (b) on day 5, the cell culture medium is supplemented with asparagine to a concentration of 4.8 mM or 6.9 mM, in addition to any asparagine already present in the cell culture medium; and
    (c) on day 7 and/or day 10, the cell culture medium is supplemented with asparagine to a concentration of 4.8 mM or 1.7 mM, in addition to any asparagine already present in the cell culture medium.

12. The method of claim 2, wherein on day 3, the cell culture medium is supplemented with iron to a concentration of between 0.5 mg/L and 2.0 mg/L, in addition to any iron already present in the cell culture medium.

13. The method of claim 2, wherein on day 3, the cell culture medium is supplemented with iron to a concentration of 0.9 mg/L or 1.5 mg/L, in addition to any iron already present in the cell culture medium.

14. The method of claim 2, wherein the cell culture medium is supplemented with iron to a concentration of between 1.0 mg/L and 4.0 mg/L on one or more days selected from the group consisting of day 5, day 7, and day 10, in addition to any iron already present in the cell culture medium.

15. The method of claim 2, wherein the cell culture medium is supplemented with iron to a concentration of 1.7 mg/L to 3.0 mg/L on one or more days selected from the group consisting of day 5, day 7, and day 10, in addition to any iron already present in the cell culture medium.

16. The method of claim 2, wherein the cell culture medium is serum-free and/or protein-free.

17. The method of claim 2, wherein the cell culture medium is supplemented with iron together with feed components in a feed medium.

18. The method of claim 2, wherein the host cell is a CHO cell.

19. The method of claim 2, wherein the cell culture method is carried out in a 3.5 L, 2800 L, 5000 L, or 15,000 L bioreactor.

20. The method of claim 2, further comprising supplementing the cell culture medium with manganese and/or glucose.

21. The method of claim 2, wherein the cell culture medium comprises an energy source, essential amino acids, vitamins, and/or trace elements.

22. The method of claim 2, wherein the protein is
    (a) tumor necrosis factor alpha (TNFα) binding protein;
    (b) an antibody;
    (c) adalimumab, infliximab, etanercept, or a biosimilar thereof; or
    (d) adalimumab or a biosimilar thereof having:
        (i) a light chain sequence having at least 90% identity with SEQ ID NO:1 and a heavy chain sequence having at least 90% identity with SEQ ID NO:2;
        (ii) a light chain sequence having at least 95% identity with SEQ ID NO:1 and a heavy chain sequence having at least 95% identity with SEQ ID NO:2;
        (iii) a light chain sequence of SEQ ID NO:1 and a heavy chain sequence of SEQ ID NO:2;
        (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8;
        (v) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8;
        (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or
        (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.

* * * * *